United States Patent [19]

Steel

[11] 3,937,073

[45] Feb. 10, 1976

[54] METHOD OF NON-DESTRUCTIVELY TESTING ALUMINUM-TO-COPPER WELDS

[75] Inventor: Robert B. Steel, Glen Mills, Pa.

[73] Assignee: General Electric Company, Philadelphia, Pa.

[22] Filed: Feb. 20, 1975

[21] Appl. No.: 551,556

[52] U.S. Cl. ................................................ 73/101
[51] Int. Cl.² ........................................ G01N 3/24
[58] Field of Search ............ 73/88 R, 88 B, 101, 67, 73/69

[56] References Cited
UNITED STATES PATENTS
3,782,183  1/1974  O'Connor et al. ................. 73/100

OTHER PUBLICATIONS
Hartbower et al., "Acoustic Emission ..... Cracking" from Acoustic Emission, ASTM STP 505, 1972, pp. 187-221.

*Primary Examiner*—Jerry W. Myracle
*Attorney, Agent, or Firm*—J. Wesley Haubner; William Freedman

[57] ABSTRACT

Discloses a method of non-destructively testing an aluminum-to-copper butt weld in a bar comprising an aluminum section and a copper section joined together by said weld. Forces are applied to the bar in such a manner that the weld is subjected to total stresses that are at least 80 percent, and preferably at least 90 percent, shear stresses. An acoustic emission signal is produced by the stresses at the weld, and this signal is sensed by a suitable transducer to provide an indication of weld quality.

12 Claims, 4 Drawing Figures

U.S. Patent Feb. 10, 1976 3,937,073
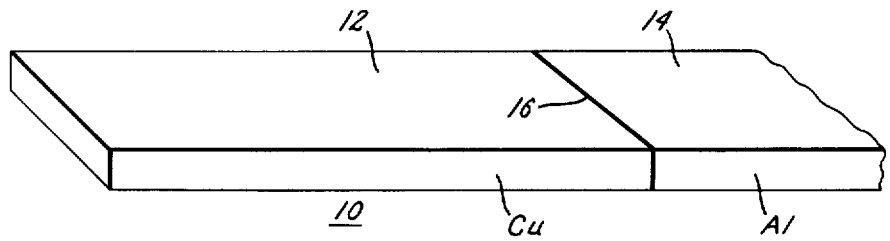
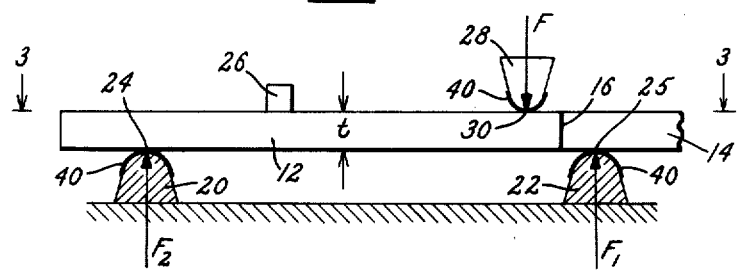
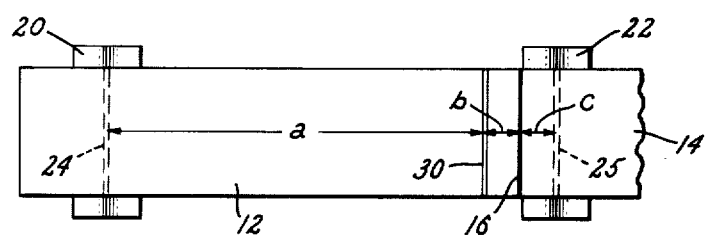
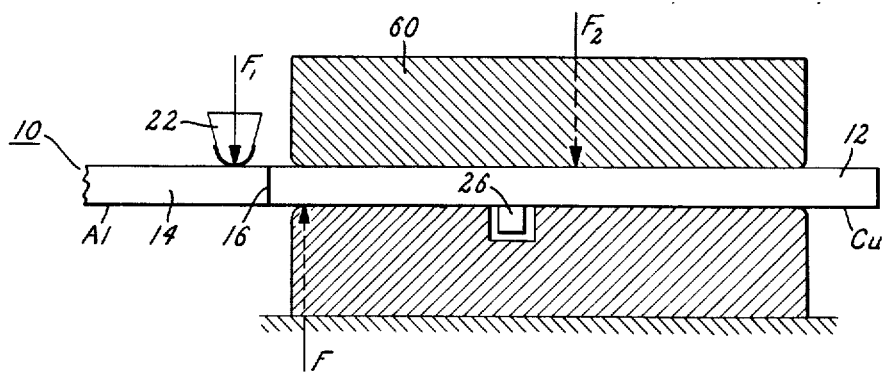

METHOD OF NON-DESTRUCTIVELY TESTING ALUMINUM-TO-COPPER WELDS

BACKGROUND

This invention relates to a method of non-destructively testing aluminum-to-copper welds and, more particularly, to a method of performing such testing by acoustic emission techniques.

When aluminum and copper parts are flash butt welded together, small quantities of relatively brittle copper-aluminum intermetallic compounds are usually formed at the joint interface. The quality of the weld depends to a large extent upon the thickness and dispersion of this deposit of intermetallic compounds. If this deposit is in the form of a continuous and relatively thick layer, the joint will be embrittled to such an extent that it may not be reliable under actual working conditions.

Heretofore, such joints have typically been tested by subjecting representative samples to a destructive bend test, referred to hereinafter as a 90°–180° bend test. In this bend test, a sample, in the form of a bar comprising copper and aluminum sections joined together by such a weld, is first bent at the weld joint until one section is angularly displaced by 90° from the other and is then reversely bent until said one section is at 180° to its previously-displaced position. If the sample can withstand such bending without significant debonding at the weld joint (e.g., less than 30% debonding), the weld is considered to have passed the test. But if significant debonding (i.e., 30 percent or more) does occur, a failure is indicated.

This bend test reveals much information on the thickness and distribution of the intermetallic compounds at the interface. Also, extensive testing has given a good correlation between bond test sampling and the reliability of similar welds throughout the anticipated lifetime of identical bars made in the same way as the tested bar.

But the destructive nature of the 90°–180° bend test is a definite disadvantage. The test specimen is rendered unusable by such test, and any bar that is to be actually used in a working environment cannot be subjected to an actual bend test.

SUMMARY

An object of my invention is to provide a highly reliable non-destructive test that can be used for evaluating the quality of aluminum-to-copper butt weld joints.

Another object is to provide a test of this character which utilizes acoustic emission techniques, performed in such a way as to limit interfering background noises to a low level.

In carrying out my invention in one form, I provide a bar comprising an aluminum section and a copper section joined together by a butt weld extending transversely of the bar. I non-destructively test this weld by applying to the bar at spaced-apart locations three separate forces that load the weld primarily in shear to a stress level of at least several thousand pounds per square inch. The forces are applied in such a manner that at least 80 percent, and preferably at least 90 percent, of the total stresses at the weld are shear stresses. The stresses thus developed at the weld create an acoustic emission signal which is propogated along the length of the bar. This acoustic emission signal is sensed by a transducer, and the output of the transducer provides an indication of the quality of the weld.

BRIEF DESCRIPTION OF DRAWING

For a better understanding of the invention, reference may be had to the following description taken in conjunction with the accompanying drawing, wherein:

FIG. 1 is perspective view of a bar haivng a weld that is to be tested in accordance with the present invention.

FIG. 2 is a partially schematic side elevational view illustrating an acoustic emission testing technique embodying one form of my invention.

FIG. 3 is a plan view of certain of the parts of FIG. 2 taken along the line 3—3 of FIG. 2.

FIG. 4 schematically illustrates modified apparatus for practicing one form of the invention.

DETAILED DESCRIPTION OF PREFERRED EMBODIMENT

Referring now to FIG. 1, there is shown a conductor 10 of bar form comprising a first section 12 of copper and a second section 14 of aluminum. The two sections are joined together by means of an aluminum-to-copper butt weld 16 made by a conventional flash welding technique. The exterior surfaces of the bar in the immediate region of weld 16 have been suitably machined to remove the flash, or projecting metal, that typically is formed at the weld periphery by flash welding.

By way of background, this flash welding technique is practiced by first locating the ends of the copper and aluminum parts in spaced relationship and then slowly moving the ends toward each other. While this is being done, the ends are heated by a succession of electric arcs between the ends which increase in frequency and current magnitude as the surfaces approach each other. At about the time the ends touch each other, the force moving the parts together is abruptly increased, producing a forging pressure that unites the parts. The forging pressure ejects slags, oxides, and molten metal from the joint interface, thus cleansing the interface; but a small amount of copper-aluminum intermetallic compounds usually remains in the joint at the interface.

As stated hereinabove, the quality of the joint depends to a large extent upon the thickness and dispersion of this deposit of intermetallic compounds. These intermetallic compounds are brittle, and if the deposit is continuous and relatively thick, the joint will be unduly embrittled.

As pointed out hereinabove, an object of my invention is to provide a non-destructive test method for evaluating such a joint to determine the extent to which it has been affected by any copper-aluminum intermetallic compounds that are present therein.

This objective can be achieved by utilizing the technique depicted in FIGS. 2 and 3. More specifically, the bar 10 is first supported on two spaced-apart stationary supports 20 and 22 which are located on opposite sides of the weld 16 and respectively engage the copper section 12 and the aluminum section 14. Each of the supports has a rounded upper surface that engages the lower surface of the bar generally along a narrow band extending transversely of the bar across its full width. In FIG. 3, the double line 24 represents the band or area of engagement at support 20, and the double line 25 represents the band or area of engagement at support 22. It will be noted that the bar 10 is positioned so that the weld 16 is located closely adjacent the support 22 that engages the aluminum section.

After the bar 10 is thus supported and positioned, a downward force F is applied to the bar at a point adjacent the weld 16, thereby loading the weld 16 primarily in shear. This downward force is applied through a loading nose 28, which has a rounded lower surface that makes contact with the upper surface of copper section 12 along a narrow band 30 extending transversely of the bar across its full width, as most clearly indicated in FIG. 3.

In one embodiment of the invention, used with a test sample having a cross section of 3 inches by ⅝ inch at the weld, the force F is 8,000 pounds, which produces a maximum shearing stress of about 6,400 p.s.i. and an average shearing stress of about 4,000 p.s.i. at the weld. Such loading normally will not significantly affect the mechanical properties of the weld and may therefore be considered as a non-destructive loading.

This shear loading of the weld 16 results in stress waves being generated at the weld and propogating along the length of the bar 10. For sensing these stress waves, I provide a transducer 25 which is suitably attached to the upper surface of the copper section 12 of the bar in a location spaced a few inches from the weld. Preferably, I attach the transducer with a viscous epoxy resin containing no curing agent. Other suitable attaching materials are glycerine and petroleum jelly. The surface to which the transducer is attached should be smooth, and, for this reason, among others, the transducer is not attached at the weld, where the surface is normally much rougher. The transducer is attached to the copper section instead of the aluminum one because copper is the denser material and can transmit the stress waves with less dispersion.

The transducer is preferably of a type that includes a piezo-electric element capable of converting these stress waves into an electrical signal having a frequency proportional to that of the stress waves, which signal is suitably amplified and fed to a conventional counting device for counting the resulting electrical pulses. A suitable transducer for this application is one sold by Dunegan/Endevco of San Juan Capistrano, Calif., as its Model S–140B transducer. This transducer responds to frequencies in the range of about 100 to 300 kilohertz.

The generation and propogation of the stress waves is referred to herein as acoustic emission. It is believed that this acoustic emission results from microcracking at the tips of the small islands of intermetallic compounds in the joint. It is further believed that such microcracks are arrested in the more ductile zones of the joint and will not propagate further through the interface when so arrested, thus limiting the number of acoustic emission events. But if the islands are larger and more frequently distributed throughout the interface area, such microcracks will link up and possibly further propogate, thus causing a greater number of acoustic emission events. In order to develop sufficient microcracking to produce significant acoustic emission for weld evaluation, the forces applied to the specimen should be high enough to produce at least several thousand pounds per square inch of shear stress at the weld 16. It should be understood that the microcracking produced by such shear stresses normally will not significantly affect the mechanical properties of the weld.

I have found that if more than a predetermined number of acoustic emission events are recorded by the transducer during the loading period required for the force F to build up to a predetermined level, then the evaluated weld 16 will almost always be unable to pass the destructive 90°–180° bending test described in the introductory portion of this specification. On the other hand, if the number of acoustic emission events is substantially below this predetermined value, then the evaluated weld will almost always be able to pass the bending test. In the above-described embodiment of the invention, the acoustic emission count figure distinguishing acceptable from non-acceptable welds was 75,000 over the loading period required for the force F to reach 8,000 pounds. This period is typically several seconds. In one specific embodiment, it was 10 to 15 seconds.

A surprisingly high degree of correlation has been observed between the results of the acoustic emission test under primarily-shear loads and the destructive bending test. In one series of tests involving 40 sample weld joints, 100% correlation between these two types of tests was achieved. More specifically, 22 of these 40 sample weld joints were predicted as good by the acoustic emission test, and all 22 of these predicted good joints passed the destructive bending test; whereas all 18 of the 40 welds that were predicted bad by the acoustic emission test failed to pass the destructive bending test.

It is highly desirable that no substantial deformation of the test sample occur at the loading locations (24, 25, and 30) since such deformation can be a source of extraneous acoustic emissions that detract from the accuracy of the above-described test. If the bar 10 does not make a good contact with the loading member along a substantial portion of the associated band 24, 30, or 25, as the case may be, then there is an increased chance for such deformation. To reduce the likelihood of such deformation, I cover the metal body of each of the loading members 20, 22, and 28 with a thin layer 40 of plastic material capable of deforming slightly when the load F is applied so as to produce closer conformity and better contact between the loading member and the adjacent surface of the bar. In one form of the invention, this layer 40 is applied in the form of self-adhesive Teflon tape 15 mils in thickness. Two thicknesses of such tape forming a layer 40 about 30 mils in total thickness are present on each loading member.

In the above-described test series, some of the bars 10 had a cross-section of 3 inches by ⅝ inch at the weld 16, and others had a cross-section of 4 inches by ½ inch at the weld. The distance $a$ between band 25 and weld 16 was 7/16 inch; the distance b between weld 16 and band 30 was 7/16 inch; and the distance c between bands 30 and 24 was 2⅛ to 4⅛ inches. The transducer 26 was located 1¾ to 3¾ inches from band 30. The curved upper surface of each of the supports 20 and 22 had a radius of 4 inches, and the curved surface of nose 28 had a radius of 1½ inches. These figures are presented by way of example and not limitation. It is highly desirable, however, that the distance $a + b$ between bands 25 and 30 be no more than 1.4 times the thickness $t$ of the bar; the distance $a$ between the weld 16 and band 30 be no more than 0.7 times the thickness $t$; and the distance c be at least about 2 inches.

The specific distances employed in the preceding paragraph result in approximately 94% of the total stresses at the weld being shear stresses and the remainder being bending stresses. It is important that the total stresses at the weld be at least 80% shear stresses and, preferably, at least 90% shear stresses. It is important to avoid a percentage of bending stresses higher than about 20% because bending stresses result in acoustic emission signals which may be rather inaccurate indications of the weld quality. In this regard, when a specimen such as 10 is loaded primarily in bending, flaws in the weld located near the surface of the specimen produce relatively high acoustic emission signals, whereas flaws in the weld near the center of the specimen produce relatively low acoustic emission signals. This is misleading because flaws near the surface may be less critical to weld strength than flaws at the center. Accordingly, I avoid more than the above-described small percentage of bending stresses.

I have also found that the type of loading that subjects the weld to primarily-tensile stresses is usually not satisfactory for this type of acoustic emission testing. Such tensile loading usually requires that the specimen be gripped so that tensile forces can be applied. When the required high tensile loads are applied, considerable plastic deformation typically occurs in the grip regions of the tensile specimens. Such deformation causes considerable acoustic emission activity and, hence, a very noisy background, masking the signal from the weld 16. The above-described and illustrated shear test obviates the need for any gripping of the test specimen and, thus, is largely free from the background noises resulting from gripping and associated deformation.

It is to be understood that the terms copper and aluminum, as used herein, are not intended to be limited to pure copper and pure aluminum, but are intended to have sufficient breadth to comprehend copper-base and aluminum-base alloys, respectively. The invention, in its broader aspects, is also applicable to other combinations of metals which react to form intermetallic compounds at their interface when welded together.

Referring to FIG. 2, the force F is opposed by reaction forces $F_1$ and $F_2$ at the loading members 20 and 22, respectively. The bar 10 may therefore be thought of as being acted upon by three separate forces F, $F_1$ and $F_2$ applied at the loading member locations.

Although I prefer to use a loading arrangement in which loading members 20 and 22 are stationary parts and loading member 28 is a movable part, it is to be understood that any two of these loading members could be stationary and the remaining one movable. The forces F, $F_1$ and $F_2$ applied to the bar 10 at the loading member locations will be distributed in the same manner between these locations irrespective of which loading member is the movable one.

Although the loading apparatus depicted in FIGS. 2 and 3 is a preferred form of apparatus for practicing the invention, other similar apparatus can be used. An example of such other apparatus is depicted in FIG. 4. Here the copper section 12 is clamped in a vise 60 that has its left hand edge near the weld 16. Closely adjacent the weld 16, a force $F_1$ is applied to the aluminum section 14 through a loading member 22, thus loading the weld primarily in shear. The force $F_1$ is opposed by two reaction forces which are depicted at F and $F_2$. It will be noted that these three forces correspond to correspondingly designated forces in FIG. 2. A transducer 26 is attached to the copper section of the bar 10 to sense the acoustic emission that results when the weld 16 is loaded in shear by the forces F, $F_1$, and $F_2$. The force $F_1$ is made high enough to develop a meaningful acoustic emission signal at the shear-loaded weld 16 without significantly deforming the specimen 10.

While I have shown and described particular embodiments of my invention, it will be obvious to those skilled in the art that various changes and modifications may be made without departing from my invention in its broader aspects; and I, therefore, intend in the appended claims to cover all such changes and modifications as fall within the true spirit and scope of my invention.

What I claim as new and desire to secure by Letters Patent of the United States is:

1. A method of non-destructively testing an aluminum-to-copper butt weld in a bar comprising an aluminum section and a copper section joined together by said weld, said weld extending transversely of said bar, said method comprising:
   a. applying first and second forces to the bar at spaced locations disposed relative to the bar on opposite sides of said transversely extending weld, with the weld being located closely adjacent the location at which one of said forces is applied to the aluminum section of the bar,
   b. applying to said copper section in a location adjacent said weld a third force that cooperates with said first and second forces to non-destructively load said weld primarily in shear, and said forces being sufficiently high to produce shear stresses at said weld of at least several thousand pounds per square inch, and
   c. sensing the acoustic emission signal resulting from the loading of said weld by said forces.

2. The method of claim 1 in which said sensing is performed by a transducer sensitive to stress waves resulting from application of said forces, said transducer being applied to said copper section at a point spaced from said weld.

3. The method of claim 1 in which said forces are applied to said bar through loading structures that comprise plastic surfaces contacting said bar that are capable of deforming slightly when loaded by application of said forces to said bar.

4. The method of claim 1 in which said third force is applied to said bar at a location spaced from said transversely-extending weld.

5. The method of claim 1 in which said bar has a thickness t extending in the same general direction as said forces are applied, the distance between said weld and the location at which said one force is applied to said aluminum section being no more than 0.7 t, and the distance between said weld and the location at which said third force is applied to said copper section being no more than 0.7 t.

6. The method of claim 5 in which the distance between the locations at which said second and third forces are applied is at least about 2 inches.

7. The method of claim 1 in which said forces are applied in such locations that at least 80% of the stresses developed in said weld by said forces are shear stresses.

8. The method of claim 1 in which said forces are applied in such locations that at least 90% of the stresses developed in said weld by said forces are shear stresses.

9. A method of non-destructively testing a butt weld in a bar comprising two sections of dissimilar metals joined together by said weld, said weld extending transversely of said bar, said metals being of such a nature as to react and form one or more brittle intermetallic compounds when welded together, said method comprising:

a. applying forces to said bar that subject said weld to total stresses that are at least 80 percent shear stresses, said forces being sufficiently high to produce shear stresses at said weld of at least several thousand pounds per square inch, said forces being applied in a manner that is essentially non-destructive of said bar and said weld, and b. sensing the acoustic emission signal resulting from the loading of said weld by said forces.

10. The method of claim 9 in which the forces applied to said bar subject said weld to total stresses that are at least 90 percent shear stresses.

11. The method of claim 10 in which said dissimilar metals are copper and aluminum.

12. The method of claim 9 in which said dissimilar metals are copper and aluminum.

* * * * *